US010709649B2

United States Patent
Deshayes et al.

(10) Patent No.: US 10,709,649 B2
(45) Date of Patent: Jul. 14, 2020

(54) TOPICAL SUNSCREEN EMULSIONS

(71) Applicant: DSM IP ASSETS B.V., Heerlen (NL)

(72) Inventors: Cyrille Deshayes, Kaiseraugst (CH); Christine Mendrok-Edinger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/568,557

(22) PCT Filed: Apr. 21, 2016

(86) PCT No.: PCT/EP2016/058931
§ 371 (c)(1),
(2) Date: Oct. 23, 2017

(87) PCT Pub. No.: WO2016/173927
PCT Pub. Date: Nov. 3, 2016

(65) Prior Publication Data
US 2018/0110706 A1    Apr. 26, 2018

(30) Foreign Application Priority Data
Apr. 29, 2015  (EP) .................... 15165781

(51) Int. Cl.
*A61K 8/34*  (2006.01)
*A61K 8/55*  (2006.01)
*A61Q 17/04*  (2006.01)
*A61K 8/06*  (2006.01)

(52) U.S. Cl.
CPC ............. *A61K 8/345* (2013.01); *A61K 8/06* (2013.01); *A61K 8/062* (2013.01); *A61K 8/55* (2013.01); *A61Q 17/04* (2013.01)

(58) Field of Classification Search
CPC .......... A61K 8/06; A61K 8/062; A61K 8/345; A61K 8/55; A61Q 17/04
See application file for complete search history.

(56) References Cited

U.S. PATENT DOCUMENTS

| 2002/0048593 A1* | 4/2002 | Biatry | A61K 8/02 424/401 |
| 2002/0155073 A1* | 10/2002 | Fankhauser | A61K 8/0241 424/59 |
| 2006/0171913 A1* | 8/2006 | Schroder | A61K 8/062 424/70.23 |
| 2016/0354303 A1* | 12/2016 | Pernodet | A61Q 19/00 |

FOREIGN PATENT DOCUMENTS

| DE | 10 2010 063825 | 6/2012 |
| EP | 0 711 540 | 5/1996 |
| EP | 0 884 046 | 12/1998 |
| EP | 1 522 303 | 4/2005 |
| FR | 2 899 462 | 10/2007 |
| JP | 8-225465 | 9/1996 |
| WO | WO 2005/048960 | 6/2005 |
| WO | WO 2009/138485 | 11/2009 |

OTHER PUBLICATIONS

International Search Report for PCT/EP2016/058931, dated Jun. 29, 2016, 3 pages.
"Retinol Complex", GNPD MINTEL, May 31, 2010, XP002744096.
SPF Boosters & Photostability of Ultraviolet Filters', HAPPI, Oct. 2007, p. 77-83.
Nadim A. Shaath, CTFA Cosmetic ingredient Handbook or "The Encyclopedia of Ultraviolet Filters" (ISBN: 978-1-932633-25-2).
International Cosmetic Ingredient Dictionary & Handbook by Personal Care Product Council (http://www.personalcarecouncil.org/), accessible by the online Info Base (http://online.personalcarecouncil.org/jsp/Home.jsp).
Intensified Day Moisture Cream, Mintel GNPD, www.neutrogena.com, Product ID #657607, Neutrogena USA, Los Angeles, CA, Feb. 2007.

* cited by examiner

*Primary Examiner* — Michael B. Pallay
(74) *Attorney, Agent, or Firm* — Nixon & Vanderhye P.C.

(57) ABSTRACT

The invention relates to topical sunscreen emulsion comprising an oil phase and a water phase, wherein said emulsion comprises a phosphate ester emulsifier, phytantriol and an amount of at least 1 wt.-% based on the total weight of the topical sunscreen emulsion of at least one UV-filter substance. Furthermore, the invention relates to the use of phytantriol for improving the water resistance of such topical sunscreen emulsions.

16 Claims, No Drawings

TOPICAL SUNSCREEN EMULSIONS

This application is the U.S. national phase of International Application No. PCT/EP2016/058931 filed 21 Apr. 2016, which designated the U.S. and claims priority to EP Patent Application No. 15165781.4 filed 29 Apr. 2015, the entire contents of each of which are hereby incorporated by reference.

The invention relates to topical sunscreen emulsion comprising an oil phase and a water phase, wherein said emulsion comprises a cetyl phosphate emulsifier, phytantriol and an amount of at least 1 wt.-% based on the total weight of the topical sunscreen emulsion of at least one UV-filter substance. Furthermore, the invention relates to the use of phytantriol for improving the water resistance of such topical sunscreen emulsions.

Sun care products have evolved considerably over the years. Earlier formulations were intended to protect the user from UV-B radiation as was once thought that UV-B rays were the most important contributors to wrinkling, skin disease, and skin cancer. However, more recent studies have shown that UV-A radiation is equally or even more important in the development of solar damage and skin diseases, such as lupus erythematosus and melanoma and non-melanoma skin cancer. Thus, today's focus is towards eliminating as much of UVA (320-400 nm) and/or UVB (280-320 nm) light as possible. Consequently, there's a constantly increasing need for sun care products exhibiting high SPF's (Sun Protection Factor) and high UVA protection.

Water resistance of sun care products is a key parameter for today's sunscreens and can for example be achieved by the addition of film forming polymers. These film forming polymers, however, are either not sufficiently effective and/or render the product unattractive for the end consumer due to the resulting sensory properties as such products often exhibit an oily, dull, and sticky feeling on the skin as e.g. outlined in DE 102010063825.

It was therefore the object of the invention to remedy the disadvantages of the prior art and to develop sunscreens which exhibit high SPF's as well as an improved water resistance and thus provide excellent UV-protection in the UVA and UVB range even after bathing. Furthermore, such compositions should exhibit good sensory properties, in particular without being unpleasantly sticky.

Surprisingly it has been found, that the water resistance of UV-filter substances in topical sunscreen emulsions consisting of an oil phase and a water phase can be significantly improved by the addition of phytantriol without negatively affecting the sensory properties. Furthermore, such compositions exhibited relatively low viscosities, i.e. viscosities in the range of 700-2000 mPas (measured with Advanced Rheometer AR 550+ with SST ST 40 mm plate at 25° C. and a shear rate of 10 1/s) which allows the formulation of sprayable products.

Thus, in one embodiment the invention relates to topical sunscreen emulsions comprising an oil phase and a water phase, wherein said emulsion comprises a cetyl phosphate emulsifier, phytantriol and an amount of at least 1 wt.-% based on the total weight of the topical sunscreen emulsion of at least one UV-filter substance.

In another aspect, the invention relates to the use of phytantriol for increasing the water resistance of a topical sunscreen emulsion comprising at least one UV-filter substance.

In a further aspect the invention relates to a method for increasing the water resistance of at least one UV-filter substance in a topical sunscreen emulsion, said method comprising the addition of phytantriol into said topical sunscreen emulsion and, preferably, observing or appreciating the result.

The amount of phytantriol to be used in the topical sunscreen emulsions according to the invention should be selected such in order to achieve the stated results. Particular advantageous is a concentration of at least 0.05 wt.-% of phytantriol based on the total weight of the topical sunscreen emulsion. Preferably in all embodiments of the present invention the amount of phytantriol is, however, selected in the range of 0.1 to 3 wt.-%, more preferably in the range of 0.2 to 2 wt.-% and most preferably in the range of 0.3 to 1.5 wt.-% based on the total weight of the topical sunscreen emulsion.

In all embodiments of the invention, the amount of the UV-filter substances (i.e. the sum of all UV-filter substances present in the topical sunscreen emulsion) is preferably selected in the range of 1 to 40 wt.-%, more preferably in the range of 5 to 35 wt.-% and most preferably in the range of 10 to 30 wt.-% based on the total weight of the topical sunscreen emulsion.

In all embodiments of the invention, the amount of the cetyl phosphate emulsifier is preferably selected in the range of 0.1 to 5 wt.-%, more preferably in the range of 0.25 to 2 wt.-% and most preferably in the range of 0.3 to 1 wt.-% based on the total weight of the topical sunscreen emulsion.

Suitable UV-filter substances according to the invention are UVA, UVB and/or broadspectrum UV-filter substances which are or can be used as cosmetically acceptable UVA, UVB or broadspectrum UV-filter substances. Such UV-filter substances are e.g. listed in the CTFA Cosmetic ingredient Handbook or "The Encyclopedia of Ultraviolet Filters" (ISBN: 978-1-932633-25-2) by Nadim A. Shaath.

The UV-filter substances may be organic or inorganic compounds. Exemplary UVA, UVB and/or broadspectrum UV-filter substances encompass dibenzoylmethane derivatives such as e.g. butyl methoxydibenzoylmethane (PARSOL® 1789); acrylates such as e.g. octocrylene (PARSOL® 340); camphor derivatives such as e.g. 4-methyl benzylidene camphor (PARSOL® 5000) or terephthalylidene dicamphor sulfonic acid (Mexoryl® SX); cinnamate derivatives such as e.g. ethylhexyl methoxycinnamate (PARSOL® MCX) or isoamyl methoxycinnamate; p-aminobenzoic acid derivatives such as e.g. p-aminobenzoic acid or 2-ethylhexyl p-dimethylaminobenzoate; benzophenones such as e.g. benzophenone-3, benzophenone-4, 2,2',4,4'-tetrahydroxy-benzophenone or 2,2'-dihydroxy-4,4'-dimethoxybenzophenone; esters of benzalmalonic acid such as e.g. di-(2-ethylhexyl) 4-methoxybenzalmalonate; organosiloxane compounds carrying chromophore groups such as e.g. polysilicone-15 (PARSOL® SLX) or drometrizole trisiloxane (Mexoryl® XL); imidazole derivatives such as e.g. 2-phenyl benzimidazole sulfonic acid and salts thereof such as e.g. its sodium- or potassium salts (PARSOL® HS); salicylate derivatives such as e.g. ethylhexyl salicylate (PARSOL® EHS, Neo Heliopan® OS), isooctyl salicylate or homosalate (PARSOL® HMS, Neo HeHopan® HMS); triazine derivatives such as e.g. ethylhexyl triazone (Uvinul® T-150), diethylhexyl butamido triazone (Uvasorb® HEB), bis-ethylhexyloxyphenol methoxyphenyl triazine (Tinosorb® S) or 2,4,6-tris[1,1'-biphenyl]-4-yl-1,3,5-triazine [CAS No. 31274-51-8]; Benzotriazole derivatives such as e.g. methylene bis-benzotriazolyl tetramethylbutylphenol (Tinosorb® M); encapsulated UV-filters such as e.g. encapsulated ethylhexyl methoxycinnamate (Eusolex® UV-pearls); amino substituted hydroxybenzophenones such as e.g. diethylamino hydroxybenzoyl hexyl benzoate (Aminobenzophenon, Uvinul® A Plus); benzoxazol-derivatives such as e.g. 2,4-bis-[5-1(dimethylpropyl)benzoxazol-2-yl-(4-phenyl)-imino]-6-(2-ethylhexyl)-imino-1,3,5-triazin (Uvasorb® K2A); phenylene-1,4-bis-benzimidazolsulfonic acids or salts thereof such as e.g. disodium phenyl dibenzimidazole tetrasulfonate (2,2-(1,4-phenylene)bis-(1H-benzimidazol-4,6-disulfonic acid, Neoheliopan® AP); 1,1'-(1,4-piperazinediyl)bis[1-[4-(diethylamino)-2-hydroxybenzoyl]phenyl]-methanone (CAS No. 919803-06-6); as well as Bis (butylbenzoate) diaminotriazine aminopropyltrisiloxane (CAS No. 207562-42-3).

Inorganic UV-filter substances encompass pigments such as e.g. microparticulated zinc oxide or titanium dioxide (e.g. commercially available as PARSOL® TX) The term "microparticulated" refers to a particle size from about 5 nm to about 200 nm, particularly from about 15 nm to about 100 nm. The particles may also be coated by other metal oxides such as e.g. aluminum or zirconium oxides or by organic coatings such as e.g. polyols, methicone, aluminum stearate, alkyl silane. Such coatings are well known in the art.

Preferred UVB-filter substances to be incorporated into the topical sunscreen emulsions according to the invention encompass polysilicone-15, phenylbenzimidazol sulfonic acid, octocrylene, ethylhexyl methoxycinnamate, ethyl hexylsalicylate and/or homosalate, most preferably phenyl benzimidazole sulfonic acid.

Preferred broadband UV-filter substances to be incorporated into the topical sunscreen emulsions according to the invention encompass unsymmetrical s-triazine derivatives such as in particular bis-ethylhexyloxyphenol methoxyphenyl triazine, certain benzophenones such as e.g. 2-hydroxy-4-methoxy-benzophenon, methylene bis-benzotriazolyl tetramethylbutylphenol and/or titanium dioxide.

Preferred UVA-filter substances to be incorporated into the topical sunscreen emulsions according to the invention encompass butyl methoxydibenzoylmethane, diethylamino hydroxybenzoyl hexyl benzoate, 2,4-bis-[5-1(dimethylpropyl)benzoxazol-2-yl-(4-phenyl)-imino]-6-(2-ethylhexyl)-imino-1,3,5-triazine and/or disodium phenyl dibenzimidazole tetrasulfonate, in particular butyl methoxydibenzoylmethane and/or diethylamino hydroxybenzoyl hexyl benzoate.

If the topical sunscreen emulsions comprise butyl methoxydibenzoylmethane, then they advantageously contain in addition at least one suitable photostabilizer for butyl methoxydibenzoylmethane. Besides specific UV-filters listed above which are known to a person skilled in the art to be able to photostabilize butyl methoxydibenzoylmethane, further exemplary photostabilizers encompass Polyester 8 (Polycrylene); Methoxycrylene (Solastay); diethylhexyl syringylidene malonate (Oxynex ST liquid); diethylhexyl naphthalate (Corapan TQ) as well as Benzotriazolyl Dodecyl p-Cresol (Tinogard® TL) without being limited thereto. An overview on such photostabilizers is e.g. given in 'SPF Boosters & Photostability of Ultraviolet Filters', HAPPI, October 2007, p. 77-83 which is included herein by reference. These photostabilizers are generally used in an amount of 0.05 to 10 wt.-% with respect to the total weigh of the topical sunscreen emulsion.

In a particular preferred embodiment the topical sunscreen emulsions according to the invention comprise at least 2, more preferably at least 3, most preferably at least 4 different UV-filter substances. Advantageously, the topical sunscreen emulsions according to the invention, in addition, comprise at least one UV-B filter substance and at least one UVA-filter substance.

In a particular advantageous embodiment, the at least one UV-filter substance present in the topical sunscreen emulsions according to the invention is selected from the group consisting of polysilicone-15, phenylbenzimidazol sulfonic acid, octocrylene, ethylhexyl methoxycinnamate, ethyl hexylsalicylate, homosalate, bis-ethylhexyloxyphenol methoxyphenyl triazine, methylene bis-benzotriazolyl tetramethylbutylphenol, titanium dioxide, butyl methoxydibenzoylmethane, diethylamino hydroxybenzoyl hexyl benzoate, disodium phenyl dibenzimidazole tetrasulfonate as well as mixtures thereof.

In a particular preferred embodiment, the at least one UV-filter substances is selected from the group consisting of butyl methoxydibenzoylmethane, phenyl benzimidazol sulfonic acid, polysilicone-15, octocrylene, homosalate, ethylhexyl salicylate, methylene bis-benzotriazolyl tetramethylbutylphenol as well as mixtures thereof.

Most preferred in all embodiments of the present invention the compositions comprises always phenyl benzimidazole sulfonic acid, optionally in combination with at least one further UV-filter substance with the preferences as outlined herein.

In an even more preferred embodiment, the topical sunscreen emulsions according to the invention comprise either a mixture of butyl methoxydibenzoylmethane, phenylbenzimidazol sulfonic acid, octocrylene, homosalate, and ethylhexyl salicylate or a mixture of butyl methoxydibenzoylmethane, phenylbenzimidazol sulfonic acid, octocrylene, and methylene bis-benzotriazolyl tetramethylbutylphenol as sole UV-filter substances. In this case the total amount of butyl methoxydibenzoylmethane, octocrylene, homosalate, methylene bis-benzotriazolyl tetramethylbutylphenol and ethylhexyl salicylate preferably sums up to 20 to 30 wt.-%, whereas the total amount of phenylbenzimidazol sulfonic acid is selected in the range of 1 to 3 wt.-%.

The UV-filter substances are incorporated either in the water or in oil phase of the topical sunscreen emulsion, depending if they are water or oil (fat) soluble/miscible UV filter substances. They may even be added to the final emulsion by standard methods known to a person skilled in the art.

Particular suitable cetyl phosphate emulsifiers according to the present invention encompass Cetyl Phosphate, DEA-Cetyl Phosphate, Potassium cetyl phosphate, and mixtures thereof. A particular preferred phosphate ester emulsifiers to be used in the topical sunscreen emulsions according to the invention is preferably potassium cetyl phosphate is e.g. commercially available as Amphisol® K at DSM Nutritional Products Ltd Kaiseraugst.

The term "topical" as used herein is understood to mean external application to keratinous substances, such as in particular the skin around the eyes.

As the topical sunscreen emulsions according to the invention are intended for topical application, they comprise a cosmetically acceptable carrier i.e. a physiologically acceptable medium which is compatible with keratinous substances, such as in particular the skin. Thus, the term cosmetically acceptable carrier refers to all cosmetic carriers and/or excipients and/or diluents conventionally used in topical sunscreen emulsions.

The topical sunscreen emulsions of the invention can also contain further conventional cosmetic adjuvants and additives, such as preservatives/antioxidants, fatty substances/oils, water, organic solvents, silicones, thickeners, softeners, emulsifiers, antifoaming agents, aesthetic components such as fragrances, emulsifiers, fillers, sequestering agents, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the invention, the topical sunscreen emulsions according to the invention may comprise further cosmetically active ingredients conventionally used in topical sunscreen emulsions. Exemplary active ingredients encompass skin lightening agents; agents for the treatment of hyperpigmentation; agents for the prevention or reduction of inflammation; firming, moisturizing, soothing, and/or energizing agents as well as agents to improve elasticity and skin barrier.

Examples of cosmetic carriers, excipients, ingredients, adjuvants, diluents and additives commonly used in the skin care industry, which are suitable for use in the compositions of the invention, are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the cosmetic adjuvants, diluents and additives can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

The topical sunscreen emulsions according to the invention may be in the form of an oil-in-water (O/W), a water-in-oil (W/O) type, a silicone-in-water (Si/W), or a water-in-silicone (W/Si) emulsion. It can also be in the form of a PIT-emulsion, a multiple emulsion (e.g. oil-in-water-in oil (O/W/O) or water-in-oil-in-water (W/O/W)) or a pickering emulsion, which can of course also be in the form of a micro-emulsion.

The amount of the oil phase present in the topical sunscreen emulsions according to the invention is advantageously at least 10 wt.-%. Preferably the amount of the oil phase in all embodiments of the present invention is selected in the range of 10 to 60 wt.-%, more preferably in the range of 20 to 50 wt.-% and most preferably in the range of 25 to 40 wt.-% based on the total weight of the topical sunscreen emulsion.

It is well understood that the oil phase encompasses the therein contained cosmetic oils as well as any oil (fat) soluble or miscible UV-filter substances.

In a particular advantageous embodiment the oil phase encompasses at least 12 wt.-%, more preferably at least 20 wt.-% such as most preferably about 25 wt.-% based on the total weight of the topical sunscreen emulsion of oil soluble or miscible UV-filter substances. Even more preferably these UV-filter substances are selected from the group consisting of polysilicone-15, octocrylene, ethylhexyl methoxycinnamate, ethyl hexylsalicylate, homosalate, bis-ethylhexyloxyphenol methoxyphenyl triazine, butyl methoxydibenzoylmethane, diethylamino hydroxybenzoyl hexyl benzoate as well as mixtures thereof, such as in particular from ethyl hexylsalicylate, homosalate, butyl methoxydibenzoylmethane and octocrylene.

Particularly suitable cosmetic oils to be incorporated into the oil phase of the topical sunscreen emulsions of the invention encompass Acetyl Tributyl Citrate, Bruxus (Jojoba Oil) Chinensis, Butylene Glycol Cocoate, Butylene Glycol Dicaprylate/Dicaprate, C12-13 Alkyl Ethylhexanoate, C12-13 Alkyl Lactate, C12-15 Alkyl Benzoate (and) Dipropylene Glycol Dibenzoate (and) PPG-15 Stearyl Ether Benzoate, C12-C15 alkyl benzoate [CAS 68411-27-8], C16-17 Alkyl Benzoate, Caprylic/Capric Triglyceride, Caprylyl Pyrrolidone, Cetearyl Isononanoate, Cetearyl Octanoate, Coco Caprylate/Caprate, Coco-Caprylate, Cocoglyceride, Cyclomethicone, Decyl Oleate, Dibutyl Adipate, Di-C12-13 Alkyl Malate, Di-C12-13 Alkyl Tartrate, Dicaprylyl Carbonate, Dicaprylyl Ether, Dicaprylyl Maleate, Diethyl Adipate, Diethyl Phthalate, diethylene glycol, Diethylhexyl 2,6-Naphthalate, Diethylhexyl Adipate, Diethylhexyl Carbonate, Diethylhexyl Malate, Diethylhexyl Maleate, Diethylhexyl Succinate, Diethylhexylcyclohexane, Diisobutyl Adipate, Diisopropyl Adipate, Diisopropyl Sebacate, Diisostearyl Malate, Dimethicone, Dimethyl Capramide, Di-PPG-2 Myreth-10 Adipate, Di-PPG-3 Myristyl Ether Adipate, Dipropylene Glycol Dibenzoate, Ethanol, Ethyl Butylacetylaminopropionate, Ethylhexyl Benzoate, Ethylhexyl Ethylhexanoate, Ethylhexyl Hydroxystearate, Ethylhexyl Palmitate, Ethylhexyl Stearate, Glycereth-26, Glyceryl Trioctanoate, Hexyl laurate, Hydrogenated Polydecene, Isocetyl Salicylate, Isodecyl Isononanoate, Isodecyl Isononanoate, Isodecyl Neopentanoate, Isodecyl Neopentanoate (and) Diisopropyl Sebacate (and) Lauryl Lactate, Isodecyl Salicylate, lsoeicosane, Isohexadecane, Isononyl Isononanoate, Isopropyl C12-15-Pareth-9 Carboxylate, Isopropyl Myristate, Isopropyl Palmitate, Isopropyl Stearate, Isosorbide Dimethylether, Isostearyl Alcohol, Isostearyl Benzoate, Isostearyl Isostearate, Isotridecyl Isononanoate, Lauryl Lactate, Lauryl Pyrrolidone, Methyl Gluceth-20 Benzoate, Methylene Dimethylether, Mineral Oil, Neopentyl Glycol Diheptanoate, Octadecene/MA Copolymer and Diethylhexyl Sebacate, Octyldodecanol, Octyldodecyl Benzoate, Octyldodecyl Myristate, Octyldodecyl Neopentanoate, Oleyl Alcohol, PEG-6 Caprylic/Capric Glycerides, PEG-7 Glyceryl Cocoate, Pentaerythrityl Tetraisostearate, Persea Gratissima (Avocado) Oil, Phenethyl Benzoate, PPG-26-Buteth-26 (and) PEG-40 Hydrogenated Castor Oil, PPG-3 Myristyl Ether, Propylene Glycol Dicaprylate/Dicaprate, Propylene Glycol Isostearate, Propylheptyl Caprylate, Sesamum Indicum (Sesame) Seed Oil, Squalane, Tributyl Citrate, Tri-C12-13 Alkyl Citrate, Trideceth-7, Tridecyl Salicylate, Tridecyl Trimellitate, Triethyl Citrate, Triethylhexanoin, Triisodecyl Trimellitate as well as mixtures thereof.

The amount of the water phase present in the topical sunscreen emulsions according to the invention is advantageously at least 30 wt.-%. Preferably the amount of the water phase in all embodiments of the present invention is selected in the range of 40 to 90 wt.-%, more preferably in the range of 50 to 80 wt.-% and most preferably in the range of 55 to 75 wt.-% based on the total weight of the topical sunscreen emulsion.

In another advantageous embodiment, the topical sunscreen emulsions according to the present invention in addition comprise an additional amount of ethanol. Preferably the amount of ethanol is selected in the range of 1 to 15 wt.-%, more preferably in the range of 3 to 12 wt.-% and most preferably in the range of 5 to 10 wt.-% based on the total weight of the topical sunscreen emulsion.

The topical sunscreen emulsions according to the invention can be provided, for example, in the form of a serum, a milk, a lotion, a hydrodispersion, a foundation, a cream, a creamgel, which are prepared according to the usual methods.

In one embodiment, the topical sunscreen emulsions according to the invention are advantageously in the form of an oil-in-water (O/W) emulsion comprising an oily phase dispersed in an aqueous phase in the presence of a phosphate ester emulsifier (i.e. an O/W emulsifier). The preparation of such O/W emulsions is well known to a person skilled in the art.

In a particular embodiment, the invention relates to topical sunscreen emulsions with all the definitions and preferences given herein which are in the form of an O/W emulsion comprising an oily phase dispersed in an aqueous phase. Preferably, the O/W emulsion comprise potassium cetyl phosphate alone or potassium cetyl phosphate in combination with at least one further O/W emulsifier. Preferably in all embodiments of the present invention as emulsifier potassium cetyl phosphate alone or potassium cetyl phosphate in combination with Polyglyceryl-3 Methylglucose Distearate or PEG-100 Stearate & Glyceryl Stearate is used. Most preferably potassium cetyl phosphate is used in combination with Polyglyceryl-3 Methylglucose Distearate or PEG-100 Stearate & Glyceryl Stearate wherein the amount of potassium cetyl phosphate is selected in the range of 0.25 to 1 wt.-% and the amount of Polyglyceryl-3 Methylglucose Distearate or PEG-100 Stearate & Glyceryl Stearate is selected in the range of 0.3 to 2.5 wt.-% based on the total weight of the topical sunscreen emulsion.

The topical compositions according to the invention furthermore advantageously contain at least one co-surfactant such as e.g. selected from the group of mono- and diglycerides and/or fatty alcohols. The co-surfactant is generally used in an amount selected in the range of 0.1 to 10 wt.-%, such as in particular in the range of 0.5 to 5 wt.-%, such as most in particular in the range of 1 to 3 wt.-%, based on the total weight of the composition. Particular suitable co-surfactants are selected from the list of alkyl alcohols such as cetyl alcohol (Lorol C16, Lanette 16) cetearyl alcohol (Lanette O), stearyl alcohol (Lanette 18), behenyl alcohol (Lanette 22), glyceryl stearate, glyceryl myristate (Estol 3650), hydrogenated coco-glycerides (Lipocire Na10), acrylates/C10-30 alkyl acrylate crosspolymer (Pemulen TR-2) as well as mixtures thereof.

The topical sunscreen emulsions according to the invention in general have a pH in the range of 3 to 10, preferably a pH in the range of 4 to 8 and most preferably a pH in the range of 4 to 7.5. The pH can easily be adjusted as desired with suitable acids such as e.g. citric acid or bases such as sodium hydroxide (e.g. as aqueous solution), Triethanolamine (TEA Care), Tromethamine (Trizma Base) and Aminomethyl Propanol (AMP-Ultra PC 2000) according to standard methods in the art.

The amount of the topical sunscreen emulsion to be applied to the skin is not critical and can easily be adjusted by a person skilled in the art. Preferably the amount is selected in the range of 0.1 to 3 mg/cm2 skin, such as preferably in the range of 0.1 to 2 mg/cm2 skin and most preferably in the range of 0.5 to 2 mg/cm2 skin.

The invention is further illustrated with reference to the following, non-limiting examples, in which all percentages are by weight based on total weight unless otherwise specified.

Example 1: Water Resistance 1.3 mg/cm$^2$ of the respective compositions as outlined in table1-6 were applied to 4 PMMA plates (Schönberg, 5 μm) and the plates were dried at RT for 30 min. Afterwards the initial in vitro SPF (Sun Protection Factor) were determined with a Labsphere UV 2000 with 9 measurement points per plate. Then the plates were immersed into a flask filled with 4 l water (bi-distilled) for 20 min while the water was stirred with a paddle agitator at 150 1/min at 30° C. water temperature (The plates were attached at the edge of the flask with a clothespin, such that the side covered with the composition was directed into the flask). Afterwards the plates were dried at 40° C. for 30 min. The immersion/drying procedure was repeated once. After final drying the in-vitro SPF was measured again and the water resistance was calculated as % WR=[(SPF after immersion−1/(SPF initial−1)]*100 and the Δ water resistance as [(% WR of sample with phytantriol)−(% WR of Sample without phytantriol)/(% WR of sample with phytantriol)]*100% Each composition was tested separately on 4 plates.

The water resistance for each composition was determined as mean value from the 4 plates.

R-1 to R-7=Respective reference example without Phytantriol

I-1 to I-9=Examples according to the invention

TABLE 1

O/W emulsion with Amphisor ® K as sole emulsifier

| | | Formulation | | |
|---|---|---|---|---|
| | | R-1 | I-1 | I-2 |
| Tradename/INCI | | Wt.-% | | |
| Aqua dem. | Water | Ad 100 | Ad 100 | Ad 100 |
| Parsol HS | Phenylbenzimidazol sulfonic acid | 2.00 | 2.00 | 2.00 |
| Tris Amino Ultra PC | Tromethamine | 1.00 | 1.00 | 1.00 |
| Viscarin PC 209 | Chondrus Crispus | 0.25 | 0.25 | 0.25 |
| Glycerin 99.5% | Glycerin | 5.00 | 5.00 | 5.00 |
| Edeta BD | Disodium EDTA | 0.10 | 0.10 | 0.10 |
| Phytantriol | Phytantriol | | 0.50 | 1.00 |
| Parsol 1789 | Butyl Methoxy-dibenzoylmethane | 4.00 | 4.00 | 4.00 |
| Parsol 340 | Octocrylene | 6.00 | 6.00 | 6.00 |
| Parsol HMS | Homosalate | 10.00 | 10.00 | 10.00 |
| Parsol EHS | Ethylhexyl Salicylate | 5.00 | 5.00 | 5.00 |
| DUB VCI 10 | Isodecyl Neopentanoate | 2.00 | 2.00 | 2.00 |
| AMPHISOL ® K | Potassium Cetyl Phosphate | 0.95 | 0.95 | 0.95 |
| Lanette 16 | Cetyl Alcohol | 1.15 | 1.15 | 1.15 |
| Ethanol | Alcohol | 6.00 | 6.00 | 6.00 |
| Euxyl PE 9010 | Phenoxyethanol, Ethylhexylglycerin | 1.00 | 1.00 | 1.00 |
| in vitro SPF initial | | 40 | 57 | 44 |
| in vitro SPF after immersion | | 12 | 25 | 26 |
| Water Resistance | | 28% | 42% | 59% |
| Δ water Resistance vs R-1 | | | +50% | +110% |
| Viscosity | | 612 | 653 | 952 |

TABLE 2

O/W emulsion with 1.1 wt.-% Tego Care 450 & 0.5 wt.-% Amphisol ® K

| | | Formulation | |
|---|---|---|---|
| | | R-2 | I-3 |
| Tradename/INCI | | Wt.-% | |
| Aqua dem. | Water | Ad 100 | Ad 100 |
| Parsol HS | Phenylbenzimidazol sulfonic acid | 2.00 | 2.00 |
| Tris Amino PC | Ultra Tromethamine | 1.10 | 1.00 |
| Viscarin PC 209 | Chondrus Crispus | 0.20 | 0.20 |
| Glycerin 99.5% | Glycerin | 5.00 | 5.00 |
| Edeta BD | Disodium EDTA | 0.10 | 0.10 |
| Phytantriol | Phytantriol | | 1.00 |
| Parsol 1789 | Butyl Methoxydibenzoylmethane | 4.00 | 4.00 |
| Parsol 340 | Octocrylene | 6.00 | 6.00 |
| Parsol HMS | Homosalate | 10.00 | 10.00 |
| Parsol EHS | Ethylhexyl Salicylate | 5.00 | 5.00 |
| DUB VCI 10 | Isodecyl Neopentanoate | 2.00 | 2.00 |
| AMPHISOL ® K | Potassium Cetyl Phosphate | 0.50 | 0.50 |
| Tego Care 450 | Polyglycetyl-3 Methylglucose Distearate | 1.10 | 1.10 |
| Lanette 16 | Cetyl Alcohol | 1.15 | 1.15 |
| Ethanol | Alcohol | 6.00 | 6.00 |
| Euxyl PE 9010 | Phenoxyethanol, Ethylhexylglycerin | 1.00 | 1.00 |
| | in vitro SPF initial | 39 | 40 |
| | in vitro SPF after immersion | 12 | 24 |
| | Water Resistance | 29% | 58% |
| | Δ water Resistance vs R-2 | | +100% |
| | Viscosity (mPas) | 1849 | 772 |

The respective formulation without phytantriol and Amphisol ® K exhibited a viscosity of 2044 mPas and was instable.

TABLE 4

O/W emulsion with 2.0 wt.-% Tego Care 450 & 0.5 wt.-% Amphisol ® K

| | | Formulation | |
|---|---|---|---|
| | | R-4 | I-6 |
| Tradename/INCI | | Wt.-% | |
| Aqua dem. | Water | Ad 100 | Ad 100 |
| Parsol HS | Phenylbenzimidazol sulfonic acid | 2.00 | 2.00 |
| Tris Amino Ultra PC | Tromethamine | 1.00 | 1.00 |
| Viscarin PC 209 | Chondrus Crispus | 0.20 | 0.20 |
| Glycerin 99.5% | Glycerin | 5.00 | 5.00 |
| Edeta BD | Disodium EDTA | 0.10 | 0.10 |
| Phytantriol | Phytantriol | | 1.00 |
| Parsol 1789 | Butyl Methoxydibenzoylmethane | 4.00 | 4.00 |
| Parsol 340 | Octocrylene | 6.00 | 6.00 |
| Parsol HMS | Homosalate | 10.00 | 10.00 |
| Parsol EHS | Ethylhexyl Salicylate | 5.00 | 5.00 |
| DUB VCI 10 | Isodecyl Neopentanoate | 2.00 | 2.00 |
| AMPHISOL ® K | Potassium Cetyl Phosphate | 0.50 | 0.50 |
| Tego Care 450 | Polyglycetyl-3 Methylglucose Distearate | 2.00 | 2.00 |
| Lanette 16 | Cetyl Alcohol | 1.15 | 1.15 |
| Ethanol | Alcohol | 6.00 | 6.00 |
| Euxyl PE 9010 | Phenoxyethanol, Ethylhexylglycerin | 1.00 | 1.00 |
| | in vitro SPF initial | 59 | 43 |
| | in vitro SPF after immersion | 10 | 14 |
| | Water Resistance | 15% | 30% |
| | Δ water Resistance vs R-4 | | +100% |
| | Viscosity (mPas) | 759 | 1125 |

The respective formulation without Amphisol ® K and phytantriol exhibited a viscosity of 2372 and was instable.

TABLE 3

O/W emulsion with 0.55 wt.-% Tego Care 450 & 1 wt.-% Amphisol ® K

| | | Formulation | | |
|---|---|---|---|---|
| | | R-3 | I-4 | I-5 |
| Tradename/INCI | | Wt.-% | | |
| Aqua dem. | Water | Ad 100 | Ad 100 | Ad 100 |
| Parsol HS | Phenylbenzimidazol sulfonic acid | 2.00 | 2.00 | 2.00 |
| Tris Amino Ultra PC | Tromethamine | 1.00 | 1.00 | 1.00 |
| Viscarin PC 209 | Chondrus Crispus | 0.20 | 0.20 | 0.20 |
| Glycerin 99.5% | Glycerin | 5.00 | 5.00 | 5.00 |
| Edeta BD | Disodium EDTA | 0.10 | 0.10 | 0.10 |
| Phytantriol | Phytantriol | | 0.50 | 1.00 |
| Parsol 1789 | Butyl Methoxydibenzoylmethane | 4.00 | 4.00 | 4.00 |
| Parsol 340 | Octocrylene | 6.00 | 6.00 | 6.00 |
| Parsol HMS | Homosalate | 10.00 | 10.00 | 10.00 |
| Parsol EHS | Ethylhexyl Salicylate | 5.00 | 5.00 | 5.00 |
| DUB VCI 10 | Isodecyl Neopentanoate | 2.00 | 2.00 | 2.00 |
| AMPHISOL ® K | Potassium Cetyl Phosphate | 1.00 | 1.00 | 1.00 |
| Tego Care 450 | Polyglycetyl-3 Methylglucose Distearate | 0.55 | 0.55 | 0.55 |
| Lanette 16 | Cetyl Alcohol | 1.15 | 1.15 | 1.15 |
| Ethanol | Alcohol | 6.00 | 6.00 | 6.00 |
| Euxyl PE 9010 | Phenoxyethanol, Ethylhexylglycerin | 1.00 | 1.00 | 1.00 |
| | in vitro SPF initial | 49.2 | 49.4 | 49.9 |
| | in vitro SPF after immersion | 7.5 | 14.2 | 34.0 |
| | Water Resistance | 13% | 27% | 67% |
| | Δ water Resistance vs R-3 | | +108% | +415% |
| | Viscosity | 512 | 1535 | 734 |

TABLE 5

O/W emulsion with 1.1 wt.-% Arlacel & 0.5 wt.-% Amphisol ® K

| Tradename | INCI | R-5 Wt.-% | I-7 Wt.-% |
|---|---|---|---|
| Aqua dem. | Water | Ad 100 | Ad 100 |
| Parsol HS | Phenylbenzimidazol sulfonic acid | 2.00 | 2.00 |
| Tris Amino Ultra PC | Tromethamine | 1.10 | 1.00 |
| Viscarin PC 209 | Chondrus Crispus | 0.20 | 0.20 |
| Glycerin 99.5% | Glycerin | 5.00 | 5.00 |
| Edeta BD | Disodium EDTA | 0.10 | 0.10 |
| Phytantriol | Phytantriol | | 1.00 |
| Parsol 1789 | Butyl Methoxydibenzoylmethane | 4.00 | 4.00 |
| Parsol 340 | Octocrylene | 6.00 | 6.00 |
| Parsol HMS | Homosalate | 10.00 | 10.00 |
| Parsol EHS | Ethylhexyl Salicylate | 5.00 | 5.00 |
| DUB VCI 10 | Isodecyl Neopentanoate | 2.00 | 2.00 |
| AMPHISOL ® K | Potassium Cetyl Phosphate | 0.50 | 0.50 |
| Arlacel 165 | PEG-100 Stearate & Glyceryl Stearate | 1.10 | 1.10 |
| Lanette 16 | Cetyl Alcohol | 1.15 | 1.15 |
| Ethanol | Alcohol | 6.00 | 6.00 |
| Euxyl PE 9010 | Phenoxyethanol, Ethylhexylglycerin | 1.00 | 1.00 |
| | in vitro SPF initial | 41.4 | 46 |
| | in vitro SPF after immersion | 4.4 | 8 |
| | Water Resistance | 8% | 15% |
| | Δ water Resistance vs R-5 | | +88% |

TABLE 6

O/W emulsion with 1.1 wt.-% Tego Care 450 & 0.15 wt.-% Pemulen TR-2

| Tradename | INCI | R-6 Wt.-% | I-8 Wt.-% |
|---|---|---|---|
| Aqua dem. | Water | Ad 100 | Ad 100 |
| Parsol HS | Phenylbenzimidazol sulfonic acid | 2.00 | 2.00 |
| Tris Amino Ultra PC | Tromethamine | 1.00 | 1.00 |
| Viscarin PC 209 | Chondrus Crispus | 0.20 | 0.20 |
| Glycerin 99.5% | Glycerin | 5.00 | 5.00 |
| Edeta BD | Disodium EDTA | 0.10 | 0.10 |
| Phytantriol | Phytantriol | | 1.00 |
| Parsol 1789 | Butyl Methoxydibenzoylmethane | 4.00 | 4.00 |
| Parsol 340 | Octocrylene | 6.00 | 6.00 |
| Parsol HMS | Homosalate | 10.00 | 10.00 |
| Parsol EHS | Ethylhexyl Salicylate | 5.00 | 5.00 |
| DUB VCI 10 | Isodecyl Neopentanoate | 2.00 | 2.00 |
| Pemulen TR-2 | Acrylates/C10-30 Alkyl Acrylate Crosspolymer | 0.15 | 0.15 |
| Tego Care 450 | Polyglyceryl-3 Methylglucose Distearate | 1.10 | 1.10 |
| Lanette 16 | Cetyl Alcohol | 1.15 | 1.15 |
| Ethanol | Alcohol | 6.00 | 6.00 |
| Euxyl PE 9010 | Phenoxyethanol, Ethylhexylglycerin | 1.00 | 1.00 |
| | in vitro SPF initial | 51 | 58 |
| | in vitro SPF after immersion | 19 | 29 |
| | Water Resistance | 35% | 50% |
| | Δ water Resistance vs R-6 | | +42% |
| | Viscosity (mPas) | 7204 | 2510 |

The respective formulation without Pemulen TR-2 and phytantriol exhibited a viscosity of 2044 mPas and was instable.

TABLE 7

O/W emulsion with 2 wt.-% Amphisol K

| Tradename | INCI | R-7 Wt.-% | I-9 Wt.-% |
|---|---|---|---|
| Amphisol K | POTASSIUM CETYL PHOSPHATE | 2.00 | 2.00 |
| Lanette O | CETEARYL ALCOHOL | 1.50 | 1.50 |
| Myritol 318 | CAPRYLIC/CAPRIC TRIGLYCERIDE | 4.00 | 4.00 |
| PARSOL 1789 | BUTYL METHOXYDIBENZOYLDIMETHANE | 4.00 | 4.00 |
| PARSOL 340 | OCTOCRYLENE | 8.00 | 8.00 |
| Finsolv TN | C12-15 ALKYL BENZOATE | 5.00 | 5.00 |
| Dub Dis | DIISOPROPYL SEBACATE | 5.00 | 5.00 |
| Keltrol CG-T | XANTHAN GUM | 0.20 | 0.20 |
| Edeta BD | EDETA | 0.20 | 0.20 |
| WATER DEM. | AQUA | 52.8 | 51.8 |
| Glycerin 1,23 (86.5%) Ph. Eur. | GLYCERIN | 3.00 | 3.00 |
| Parsol HS | PHENYLBENZIMIDAZOLE SULFONIC ACID | 2.00 | 2.00 |
| Triethanolamine Care | TRIETHANOLAMINE | 1.30 | 1.30 |
| Euxyl PE 9010 | PHENOXYETHANOL, ETHYLHEXYLGLYCERIN | 1.00 | 1.00 |
| Tinosorb M | | 10.00 | 10.00 |
| Phytantriol | | | 1.00 |
| | in vitro SPF initial | 90 | 78 |
| | in vitro SPF after immersion | 12 | 61 |
| | Water Resistance | 12% | 78% |
| | Δ water Resistance vs R-7 | | +550% |
| | Viscosity (mPas) | 1840 | 2120 |

Comparative Example

Weigh the PMMA "HD6" Slides and then weight accurately 28.5 mg of the sunscreen formulation as outlined in table 8 onto the PMMA "HD6 Slides which corresponds to an amount of 1.30 mg/cm$^2$. Saturate the finger tip with the formulation. With this finger tip uniformly spread the formulation on the surface of the PMMA "HD 6" slides. Because of losing volatile components of the formulation during the weighing procedure (e.g. water, alcohol), an actual amount of 13-16 mg will remain on the slides. The amount varies depending on content of volatile formulation components. The plate is stored for 15 min at RT until the film is completely dried and a water droplet out of a pipette is applied on the plate.

Afterwards a picture was taken. The diameter (reflecting the contact angle/wetting appearance) of the water droplet was determined initially and after 2 minutes with a ruler. The higher the diameter the higher is the wettability and the higher is the wash-out rate, respectively the lower is the water resistance.

As can be retrieved from the results outlined below, the addition of phytantriol significantly reduces the wettability, which is illustrated by a reduced diameter for both formulations (Inv-A&P and R-L&P). However, the combination of Amphisol K and Phytantriol (Inv-A&P) surprisingly results in significantly superior results compared to the combination of Laureth-phophate and Phytantriol (R-L&P).

TABLE 8

| | INCI | Ref-A % | Inv-A & P % | R-L % | R-L & P % |
|---|---|---|---|---|---|
| A | Water | Ad 100 | Ad 100 | Ad 100 | Ad 100 |
| | Trilaureth-4-Phosphate | — | — | 1.10 | 1.10 |
| | Phenyl benzimidazole sulfonic acid | 2.00 | 2.00 | 2.00 | 2.00 |
| | Tromethamine | 1.00 | 1.00 | 1.00 | 1.00 |
| | Chondrus Crispus | 0.25 | 0.25 | 0.25 | 0.25 |
| | Glycerin | 5.00 | 5.00 | 5.00 | 5.00 |
| | Disodium EDTA | 0.10 | 0.10 | 0.10 | 0.10 |
| B | Phytantriol | | 1.00 | | 1.00 |
| | Butyl Methoxy-dibenzoylmethane | 4.00 | 4.00 | 4.00 | 4.00 |
| | Octocrylene | 6.00 | 6.00 | 6.00 | 6.00 |
| | Homosalate | 10.00 | 10.00 | 10.00 | 10.00 |
| | Ethylhexyl Salicylate | 5.00 | 5.00 | 5.00 | 5.00 |
| | Isodecyl Neopentanoate | 2.00 | 2.00 | 2.00 | 2.00 |
| | Potassium Cetyl Phosphate | 0.95 | 0.95 | | |
| | Cetyl Alcohol | 1.15 | 1.15 | 1.15 | 1.15 |
| 40° C. | Alcohol | 6.00 | 6.00 | 6.00 | 6.00 |
| 40° C. | Phenoxyethanol, Ethylhexylglycerin | 1.00 | 1.00 | 1.00 | 1.00 |
| | Diameter of water droplet | | | | |
| | Initial | 10 mm | 5 mm | 15 mm | 13 mm |
| | (diameter reduction) | | (−50%) | | (−13%) |
| | After 2 min | 12 mm | 6 mm | 20 mm | 16 mm |
| | (diameter reduction) | | (−50%) | | (−20%) |

The invention claimed is:

1. A topical sunscreen emulsion comprising an oil phase and a water phase, wherein the emulsion comprises:
   (i) 0.5 wt. % to 2 wt. % of potassium cetyl phosphate as an emulsifier,
   (ii) at least 1 wt. % of at least one UV-filter substance, and
   (iii) an amount of 0.5 wt. % to 1 wt. % of phytantriol sufficient to impart to the topical sunscreen emulsion an improved water resistance of 42% to 550% as compared to an identical topical sunscreen emulsion not having the phytantriol, wherein
   all weight percentages are based on the total weight of the topical sunscreen emulsion.

2. The topical sunscreen emulsion according to claim 1, wherein the at least one UV-filter substance is present in an amount of 1 to 40 wt.-%.

3. The topical sunscreen emulsion according to claim 1, wherein the at least one UV-filter substance comprises at least one UVB-filter substance and at least one UVA-filter substance.

4. The topical sunscreen emulsion according to claim 1, wherein the at least one UV-filter substance is at least one selected from the group consisting of polysilicone-15, phenylbenzimidazol sulfonic acid, octocrylene, ethylhexyl methoxycinnamate, ethyl hexylsalicylate, homosalate, bis-ethylhexyloxyphenol methoxyphenyl triazine, methylene bis-benzotriazolyl tetramethylbutylphenol, titanium dioxide, butyl methoxydibenzoylmethane, diethylamino hydroxybenzoyl hexyl benzoate, disodium phenyl dibenzimidazole tetrasulfonate and mixtures thereof.

5. The topical sunscreen emulsion according to claim 4, wherein the at least one UV-filter substance is at least one selected from the group consisting of butyl methoxydibenzoylmethane, phenylbenzimidazol sulfonic acid, octocrylene, homosalate, ethylhexyl salicylate and mixtures thereof.

6. The topical sunscreen emulsion according to claim 1, wherein the oil phase is present in the topical sunscreen emulsion in an amount of 10 to 60 wt. %, based on the total weight of the topical sunscreen emulsion.

7. The topical sunscreen emulsion according to claim 1, wherein the topical sunscreen emulsion is in the form of an oil-in-water (O/W) emulsion wherein the oil phase is dispersed in the water phase.

8. The topical sunscreen emulsion according to claim 1, wherein the composition comprises at least one additional emulsifier.

9. The topical sunscreen emulsion according to claim 8, wherein the at least one additional emulsifier is selected from polyglyceryl-3 methylglucose distearate, polyethyleneglycol-100 stearate and glyceryl stearate.

10. The topical sunscreen emulsion according to claim 1, which further comprises a co-surfactant.

11. The topical sunscreen emulsion according to claim 10, wherein the co-surfactant is cetyl alcohol and/or acrylates/C10-30 alkyl acrylate crosspolymer.

12. The topical sunscreen emulsion according to claim 2, wherein the at least one UV-filter substance is present in an amount of 5 to 35 wt. %, based on the total weight of the topical sunscreen emulsion.

13. The topical sunscreen emulsion according to claim 2, wherein the at least one UV-filter substance is present in an amount of 10 to 30 wt. %, based on the total weight of the topical sunscreen emulsion.

14. The topical sunscreen emulsion according to claim 6, wherein the oil phase is present in the topical sunscreen emulsion in an amount of 20 to 50 wt. %, based on the total weight of the topical sunscreen emulsion.

15. The topical sunscreen emulsion according to claim 6, wherein the oil phase is present in the topical sunscreen emulsion in an amount of 25 to 40 wt. %, based on the total weight of the topical sunscreen emulsion.

16. A method for increasing the water resistance of a topical sunscreen emulsion comprising at least 1 wt. % of at least one UV-filter substance and 0.5 wt. % to 2 wt. % of potassium cetyl phosphate as an emulsifier, wherein the method comprises adding to the topical sunscreen emulsion an amount of 0.5 wt. % to 1 wt. % of phytantriol sufficient to impart to the topical sunscreen emulsion an improved water resistance of 42% to 550% as compared to an identical topical sunscreen emulsion not having the phytantriol.

* * * * *